United States Patent [19]

Taylor

[11] 4,391,153

[45] Jul. 5, 1983

[54] SEGMENTED FIBER SAMPLER

[75] Inventor: Robert A. Taylor, Anderson, S.C.

[73] Assignee: The United States of America as represented by the United States Department of Agriculture, Washington, D.C.

[21] Appl. No.: 337,044

[22] Filed: Jan. 4, 1982

[51] Int. Cl.³ .............................................. G01N 3/10
[52] U.S. Cl. ................................................ 73/864.41
[58] Field of Search ..................... 73/159, 863.81, 864, 73/864.41, 864.42

[56] References Cited

U.S. PATENT DOCUMENTS 3,347,102 10/1967 Phillips ............................. 73/863.81

FOREIGN PATENT DOCUMENTS 237884 2/1961 Australia ........................... 73/864.41
141337 1/1961 U.S.S.R. ............................ 73/864.41

Primary Examiner—S. Clement Swisher
Attorney, Agent, or Firm—M. Howard Silverstein; David G. McConnell; Raymond C. Von Bodungen

[57] ABSTRACT

An apparatus for sampling staple fibers containing foreign matter is disclosed. A clamping device is provided comprising upper and lower jaws pivoted with respect to each other. The upper jaw is segmented on one end to allow for localized deflection of the individual segments when foreign material is present. On the other end a spring assembly is provided to insure proper clamping pressure during and after the taking of a sample.

2 Claims, 2 Drawing Figures

SEGMENTED FIBER SAMPLER

BACKGROUND OF THE INVENTION

1. Field of the Invention

This invention relates to a device used to gather a sample of fiber for testing purposes.

2. Description of the Prior Art

The cotton textile industry frequently requires testing of lint cotton samples for physical properties. Therefore, cotton samples must be procured from large quantities of cotton. These samples take the form of cotton beards. Conventional methods of preparing these fiber beards for length and strength involves testing equipment which is designed as a clamping device. However, heretofore, these clamping devices were designed with two rigid clamps. Specimen beards obtained with using such rigid clamping devices frequently contained holes or missing sections which deemed the samples unacceptable for use. It was generally noted that this problem was caused from localized trash or fiber lumps which, as a result of rigid jaws or clamps, prevented uniform gripping of the fiber in the formation of a beard. To overcome this problem, fibers being sampled were either blended to remove lumps and trash or repeat sampling was performed until an acceptable beard was obtained.

SUMMARY OF THE INVENTION

The instant invention solves the long standing problem of holes and missing sections in cotton staple fiber samples. The problem was due to rigid jaws on all of the sampling devices. It was discovered that this problem could be resolved by using a segmented jaw on a clamping device so that the individual segments of the jaw would deflect to compensate for foreign materials which appear non-uniformly during the process of taking cotton samples.

The preferred embodiment of the invention comprises a lower rigid jaw juxtaposed to an upper clamping jaw which is fabricated into a plurality of equal segments on one end. A means of pivoting the upper and lower jaw in relation to each other is provided. There is a spring assembly provided between the upper and lower jaws which is located on the opposite end from the segmented end. When foreign materials or trash appear in the cotton to be sampled, the segments deflect in different amounts to accommodate the local differences in fiber density and/or imbedded trash/foreign particles. Thus holes or missing sections of the cotton sample are avoided when the sample is combed out for testing. The spring assembly provides clamping pressure during and after the taking of a sample.

DESCRIPTION OF THE PREFERRED EMBODIMENTS

Figure 1:
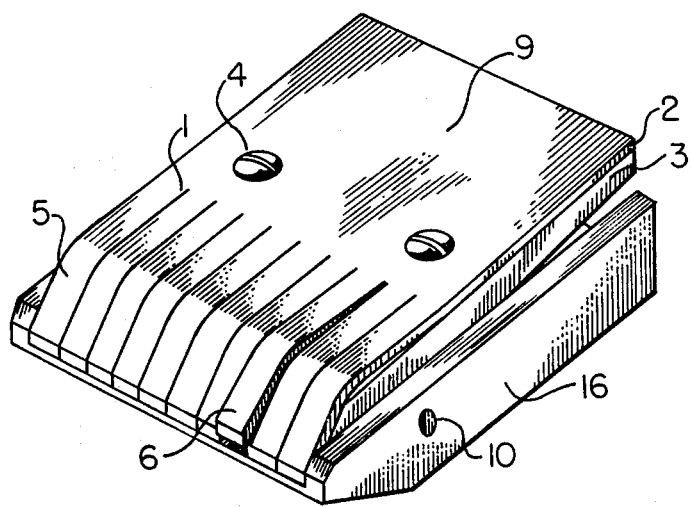
FIG. 1 is an isometric drawing of the assembled segmented fiber sampler.

In operation, a fiber sample is obtained by applying an opening force to the sampling device. A pinching force is applied to the back ends of the sampler, thus forcing open the jaws or front end of the device. The opened sampler jaws are then pressed against a large supply of fibers (such as a cotton bale) while at the same time holding open the jaws with the pinching forces at the back end. The pinching force is released after the amount of cotton sample desired is located between the opened front jaws. The sampler is then withdrawn from the supply, taking with it a small amount of cotton sample locked within the closed jaws. As the sampler is pulled away, a cotton fiber beard sample is obtained. The preparation of a sample can be manual or automatic and it involves the removal of loose fibers and trash contained within the clamped fiber sample using a wire brush. Final fiber beard preparation involves brushing the remaining fibers held within the bite of the sampler jaws to produce a parallel fiber arrangement with uniform fiber crimp for testing consistency. Fiber beard samples are then so organized and tested on special instruments designed to measure fiber length, length variability, and the flat bundle breaking strength. One can readily see the importance of getting uniform and accurate fiber samples in order to obtain good quality samples for reliable comparison. In the case of the prior art sampling devices it was this foreign material and trash which could cause non-uniform samples and thus the loss of samples and unreliable testing results. Since the top and bottom jaw of the prior art sampling devices were rigid, the trash and foreign materials would not allow the jaws to clamp down uniformly and thus the entire clamping surface was held open and the cotton or fiber sample would slip out of the grip causing either holes in the sample or missing sections. This required that the sample be discarded or unreliable test results were obtained. In the case of the preferred embodiment of the invention use of a segmented top clamping jaw avoids this problem and produces uniform samples in every case, even where trash or foreign material becomes lodged between the jaws. A uniform gripping surface is thus provided between the jaws preventing large segments or loosely held fibers from being pulled from the sampler during the combing and brushing operation of the process.

In general, the preferred embodiment comprises an upper 2 and lower 7 clamping jaw. Lower jaw 7 is rigid but upper jaw 2 is segmented on one end. A plurality of segments 5 is formed by cutting the end in equally spaced slots. Rigid lower jaw 7 has a flange 16 affixed the length of each side. Upper jaw 7 has a small flange 3 or shoulder affixed along the edge of each side. Upper jaw 2 is sized to fit loosely inside lower jaw flanges 16. The jaws are pivoted with respect to each other by means of a pivot pin 10 which goes through lower jaw side flanges 16 and through the body 3 of the upper jaw 2. A spring assembly 8 is provided at the end opposite the segmented end. This spring assembly is for pinching action to open the segmented end and hold the sample with force when being taken and later when subsequently combed with a brush into a beard and processed through the physical testing procedure. When a sample is extracted and foreign matter is present, then the segmented jaw will deflect and allow for even pressure sampling, thus avoiding holes or missing spaces.

Figure 2:
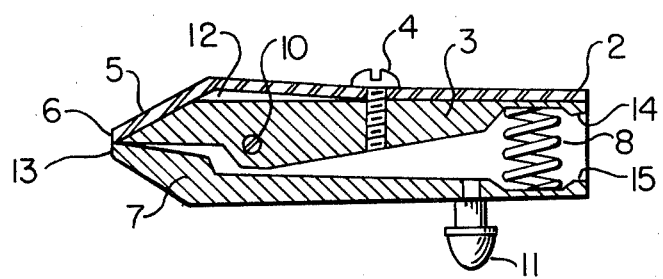
FIG. 2 is a sectional drawing of the fiber sampler showing its component parts.

Turning now to the specific embodiment of the invention wherein FIG. 1 shows the arrangement of saw cuts 1 used to divide a 2-inch-wide spring steel plate 2 into ten equal segments 5. Spring steel face plate 2 material is 1/16 inch thick and the end cuts are 0.016 in. wide. They were cut before bending. The cuts extend through and are 1⅛ in. along the plate length from the end. Other cut configurations should operate satisfactorily. However, this configuration was used for convenience of fabrication. The individual segments 5 are free to bend in different amounts 6 as fibers or trash are caught between the segment and rigid lower jaw 7. Lower jaw 7 has side flanges 16 separated sufficiently to allow upper jaw 2 to fit freely between flanges 16. Steel pivot pins 10 (⅛" dia. ×" long) are used to extend through lower jaw flanges 16 and into body 3 of the upper jaw 2 to allow free movement of the upper jaw 2 which is segmented plate assembly 2. Return springs 8 (only one shown in FIG. 2 but two or more may be p;rovided as needed) are mounted between upper jaw 2 and lower jaw 7 opposite the segmented end and in clamp base region 9 (FIG. 1) to provide the required gripping force on the fibers once a sample is taken. Spring steel plate 2 (which forms upper jaw 2) is so arranged as to produce a preset deflection of 1/16" measured at point 12 (shown in FIG. 2) in all ten of jaw segments 5 when mounted and secured to upper jaw 2 which is movable. Reset deflection 12 (FIG. 2) can be adjusted by backing off two clamping screws 4 and sliding segmented plate/upper jaw 2 in the direction of clamp base region 9. Screws 4 are provided with holes in the segmented plate 2 and are elongated ⅛" to allow for a preset deflection gap adjustment 12. Preset deflection adjustment 12 is performed prior to grinding spring plate segments 5 flush with lower jaw face 13. Preset deflection 12 is used to induce the desired level of fiber gripping force with small movement angles of upper jaw 3, thereby accurately controlling the amount of fibers sampled. Fiber sampling is performed by applying a compressive force (approximately 40 pounds) until the upper and lower jaws come in contact at points 14 and 15. The opened clamp is then moved into a fiber supply and the compressive force is released. The sampled fibers are removed from the supply, excess fibers are combed out, and the sampled fibers are straightened and aligned by brushing. Anchor pins 11 are provided for use in holding the sampler securely in automatic length and strength testing equipment.

I claim:

1. An apparatus for sampling staple fibers comprising in combination:
   (a) a rigid lower jaw;
   (b) an upper jaw juxtaposed to said lower rigid jaw, one end of said upper jaw fabricated into a plurality of segments, said segments capable of deflecting in different amounts to accommodate local differences in fiber density and/or imbedded trash/foreign particles;
   (c) means for pivoting said upper jaw in relation to said rigid lower jaw;
   (d) a spring assembly located between said upper and lower jaws, said spring assembly also located on the opposite end from the segmented end of said upper jaw to provide clamping pressure during and after the taking of a sample.

2. The apparatus of claim 1 wherein the segmented end of the upper jaw is divided into 10 equal segments.

* * * * *